US009426982B2

(12) United States Patent
Boucher, Jr. et al.

(10) Patent No.: US 9,426,982 B2
(45) Date of Patent: Aug. 30, 2016

(54) STABILIZED OIL-IN-WATER EMULSIONS INCLUDING AGRICULTURALLY ACTIVE INGREDIENTS

(75) Inventors: Raymond E. Boucher, Jr., Lebanon, IN (US); Valerie Dumontet, Oberhausbergen (FR); Frederick R. Green, III, Noblesville, IN (US); David G. Ouse, Indianapolis, IN (US); Holger Tank, Zionsville, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 799 days.

(21) Appl. No.: 12/365,694

(22) Filed: Feb. 4, 2009

(65) Prior Publication Data
US 2009/0197768 A1    Aug. 6, 2009

Related U.S. Application Data

(60) Provisional application No. 61/063,492, filed on Feb. 4, 2008, provisional application No. 61/068,529, filed on Mar. 7, 2008.

(51) Int. Cl.
*A01N 37/18* (2006.01)
*A01N 25/04* (2006.01)
*A01N 25/30* (2006.01)

(52) U.S. Cl.
CPC ............ *A01N 25/04* (2013.01); *A01N 25/30* (2013.01)

(58) Field of Classification Search
CPC ............................. A01N 25/04; A01N 25/30
USPC .......................................................... 504/363
See application file for complete search history.

(56) References Cited

U.S. PATENT DOCUMENTS

| | | |
|---|---|---|
| 5,037,653 A | 8/1991 | Dawson |
| 5,512,534 A | 4/1996 | Frisch et al. |
| 5,658,575 A | 8/1997 | Ribier et al. |
| 5,753,241 A | 5/1998 | Ribier et al. |
| 5,925,341 A | 7/1999 | Cervantes et al. |
| 5,925,364 A | 7/1999 | Ribier et al. |
| 6,039,936 A | 3/2000 | Restle et al. |
| 6,066,328 A | 5/2000 | Ribier et al. |
| 6,074,986 A * | 6/2000 | Mulqueen et al. ............ 504/361 |
| 6,120,778 A | 9/2000 | Simonnet |
| 6,126,948 A | 10/2000 | Simmonnet et al. |
| 6,199,318 B1 * | 3/2001 | Stewart et al. ................ 47/57.6 |
| 6,274,150 B1 | 8/2001 | Simonnet et al. |
| 6,335,022 B1 | 1/2002 | Simonnet et al. |
| 6,375,960 B1 | 4/2002 | Simonnet et al. |
| 6,413,527 B1 | 7/2002 | Simonnet et al. |
| 6,416,768 B1 | 7/2002 | Ravaux et al. |
| 6,419,946 B1 | 7/2002 | Simonnet et al. |
| 6,461,625 B1 | 10/2002 | Simonnet et al. |
| 6,464,990 B2 | 10/2002 | Simmonnet et al. |
| 6,541,018 B1 | 4/2003 | Simmonnet et al. |
| 6,689,371 B1 | 2/2004 | Simmonnet et al. |
| 6,902,737 B2 | 6/2005 | Quemin |
| 2002/0035182 A1 | 3/2002 | L'Alloret et al. |
| 2003/0206955 A1 | 11/2003 | Sonneville-Aubrun et al. |
| 2004/0137031 A1 | 7/2004 | Seitz et al. |
| 2006/0124598 A1 | 6/2006 | Bessoles et al. |
| 2007/0027034 A1 * | 2/2007 | Tank et al. ..................... 504/363 |

FOREIGN PATENT DOCUMENTS

| | | |
|---|---|---|
| EP | 641557 | 8/1996 |
| EP | 1063007 | 12/2000 |
| EP | 1025898 B | 1/2002 |
| EP | 1552820 A | 7/2005 |
| GB | 1 164 321 | 9/1969 |
| JP | 1439244 | 6/1976 |
| JP | 02-108602 A | 4/1990 |
| JP | 02-282302 A | 11/1990 |
| JP | 09-510180 A | 10/1997 |
| JP | 2002-536507 A | 10/2002 |
| JP | 2005-507401 A | 3/2005 |
| JP | 2007308440 | 11/2007 |
| JP | 2007308440 A | 11/2007 |
| WO | 2004017734 | 3/2004 |
| WO | 20060094978 | 9/2006 |
| WO | WO2007014386 A2 | 2/2007 |
| WO | WO 2007/053852 | 5/2007 |

OTHER PUBLICATIONS

International Search Report for Application No. PCT/US2009/033097, filed Feb. 4, 2009 (4 pages).
Written Opinion of the International Searching Authority for Application No. PCT/IS2009/033097, filed Feb. 4, 2009 (7 pages).
International Search Report for Application No. PCT/US2006/029743, filed Jul. 28, 2006 (4 pages).
Written Opinion of the International Searching Authority for Application No. PCT/US2006/029743, filed Jul. 28, 2006 (9 pages).
International Search Report for Application No. PCT/US2009/033098, filed Feb. 4, 2009 (3 pages).
Written Opinion of the International Searching Authority for Application No. PCT/US2009/033098, filed Feb. 4, 2009 (6 pages).
International Search Report for Application No. PCT/US2009/036509, filed Mar. 9, 3009; (3 pages).
Written Opinion of the International Searching Authority for Application No. PCT/US2009/036509, filed Mar. 9, 2009 (7 pages).
International Search Report for Application No. PCT/US2009/036514, filed Mar. 9, 2009 (3 pages).
Written Opinion of the International Searching Authority for Application No. PCT/US2009/036514, filed Mar. 9, 2009 (7 pages).
International Search Report for Application No. PCT/US2009/036507, filed Mar. 9, 2009 (3 pages).

(Continued)

*Primary Examiner* — Ali Soroush
*Assistant Examiner* — Danielle Sullivan
(74) *Attorney, Agent, or Firm* — Charles W. Arnett; Faegre Baker Daniels LLP

(57) ABSTRACT

The present invention relates to stable, agricultural oil-in-water emulsion compositions.

30 Claims, No Drawings

(56) References Cited

OTHER PUBLICATIONS

Written Opinion of the International Searching Authority for Application No. PCT/US2009/036507, filed Mar. 9, 2009 (7 pages).
International Searching Authority, International Search Report for PCT/US2009/033097, dated Aug. 13, 2009, 4 pages.
International Searching Authority, Written Opinion for PCT/US2009/033097, dated Aug. 13, 2009, 7 pages.
International Searching Authority, International Preliminary Report on Patentability for PCT/US2009/033097, dated Aug. 10, 2010, 8 pages.

* cited by examiner

STABILIZED OIL-IN-WATER EMULSIONS INCLUDING AGRICULTURALLY ACTIVE INGREDIENTS

CROSS-REFERENCE TO RELATED APPLICATIONS

This application claims the benefit of U.S. Provisional Patent Application Ser. No. 61/063,492, filed Feb. 4, 2008, and U.S. Provisional Patent Application Ser. No. 61/068,529, filed Mar. 7, 2008, both of which are expressly incorporated by reference herein.

FIELD OF THE INVENTION

The present invention relates to stable, agricultural oil-in-water emulsion compositions.

BACKGROUND AND SUMMARY

Concentrated oil-in water emulsions of liquid active ingredients or active ingredients dissolved in a solvent are commonly used in agricultural compositions due to certain advantages provided over other formulation types. Emulsions are water based, contain little or no solvent, allow mixtures of active ingredients to be combined into a single formulation and are compatible with a wide range of packaging material. However, there are also several disadvantages of such agricultural emulsions, namely that they are often complex formulations which require high amounts of surface-active agents for stabilization, are generally very viscous, have a tendency for Oswald ripening of the emulsion globules and separate over time. Therefore, improvements in such emulsion formulations are needed in the agricultural field.

Several oil-in-water emulsion compositions for cosmetics and dermatological applications have been described in U.S. Pat. No. 5,658,575; U.S. Pat. No. 5,925,364; U.S. Pat. No. 5,753,241; U.S. Pat. No. 5,925,341; U.S. Pat. No. 6,066,328; U.S. Pat. No. 6,120,778; U.S. Pat. No. 6,126,948; U.S. Pat. No. 6,689,371; U.S. Pat. No. 6,419,946; U.S. Pat. No. 6,541,018; U.S. Pat. No. 6,335,022; U.S. Pat. No. 6,274,150; U.S. Pat. No. 6,375,960; U.S. Pat. No. 6,464,990; U.S. Pat. No. 6,413,527; U.S. Pat. No. 6,461,625; and U.S. Pat. No. 6,902,737; all of which are expressly incorporated herein by reference. However, although these types of emulsions have found advantageous use in personal care products, these types of emulsions have not been used previously with agriculturally active compounds, which are typically present in emulsions at much higher levels than cosmetic active ingredients.

One example of an agricultural oil-in-water emulsion composition that is suitable for agriculturally active ingredients that are liquid or soluble in suitable solvents at relevant storage temperatures is disclosed in U.S. patent application Ser. No. 11/495,228, the disclosure of which is expressly incorporated by reference herein.

The present invention is related to agricultural compositions comprising an oil-in-water emulsion, the oil-in-water emulsion composition having an oil phase and water phase, the oil-in-water emulsion composition comprising an oil adapted to form oily globules having a mean particle diameter of less than 800 nanometers, a polymeric modifier that is compatible with the oil phase, at least one agriculturally active compound, at least one non-ionic lipophilic surface-active agent, at least one non-ionic hydrophilic surface-active agent, at least one ionic surface-active agent, and water.

DETAILED DESCRIPTION

One embodiment of the present invention is a novel oil-in-water emulsion composition having an oil phase and water phase, the oil-in-water emulsion composition comprising:
an oil adapted to form oily globules having a mean particle diameter of less than 800 nanometers;
a polymeric modifier being compatible with the oil phase;
at least one agriculturally active compound;
at least one non-ionic lipophilic surface-active agent,
at least one non-ionic hydrophilic surface-active agent;
at least one ionic surface-active agent; and
water.

The oil phase of the oil-in-water emulsion of the present invention utilizes either an agriculturally active compound which is in the form of an oil, or alternatively, an agriculturally active compound dissolved or mixed in an oil, to form the oily globules. An oil is by definition, a liquid which is not miscible with water. Any oil which is compatible with the agriculturally active compound may be used in the oil-in-water emulsions of the present invention. The term 'compatible' means that the oil will dissolve or mix uniformly with the agriculturally active compound and allow for the formation of the oily globules of the oil-in-water emulsion of the present invention. Exemplary oils include, but are not limited to short-chain fatty acid triglycerides, silicone oils, petroleum fractions or hydrocarbons such as heavy aromatic naphtha solvents, light aromatic naphtha solvents, hydrotreated light petroleum distillates, paraffinic solvents, mineral oil, alkylbenzenes, paraffinic oils, and the like; vegetable oils such as soy oil, rape seed oil, coconut oil, cotton seed oil, palm oil, soybean oil, and the like; alkylated vegetable oils and alkyl esters of fatty acids such as methyloleate and the like.

An agriculturally active compound is herein defined as any oil soluble compound, hydrophobic compound, or solid compound having a melting point of below about 95 degrees Celsius or less that shows some pesticidal or biocidal activity. It is understood to refer to the active compound per se when it is itself an oil or alternatively, the active compound dissolved in an oil of suitable polymeric modifier. Such compounds or pesticides include fungicides, insecticides, nematocides, miticides, termiticides, rodenticides, arthropodicides, herbicides, biocides and the like. Examples of such agriculturally active ingredients can be found in The Pesticide Manual, 12$^{th}$ Edition. Exemplary pesticides which can be utilized in the oil-in-water emulsion of the present invention include, but are not limited to, benzofuranyl methylcarbamate insecticides such as benfuracarb, and carbosulfan; oxime carbamate insecticides such as aldicarb; fumigant insecticides such as chloropicrin, 1,3-dichloropropene and methyl bromide; juvenile hormone mimics such as fenoxycarb; organophosphate insecticides such as dichlorvos; aliphatic organothiophosphate insecticides such as malathion and terbufos; aliphatic amide organothiophosphate insecticides such as dimethoate; benzotriazine organothiophosphate insecticides such as azinphos-ethyl and azinphos-methyl; pyridine organothiophosphate insecticides such as chlorpyrifos and chlorpyrifos-methyl; pyrimidine organothiophosphate insecticides such as diazinon; phenyl organothiophosphate insecticides such as parathion and parathion-methyl; pyrethroid ester insecticides such as bifenthrin, cyfluthrin, beta-cyfluthrin, cyhalothrin, gamma-cyhalothrin, lambda-cyhalothrin, cypermethrin, alpha-cypermethrin, beta-cypermethrin, fenvalerate, and permethrin; and the like.

Exemplary herbicides which can be used in the oil-in-water emulsion of the present invention include, but are not limited to: amide herbicides such as dimethenamid and dimethenamid-P; anilide herbicides such as propanil; chloroacetanilide herbicides such as acetochlor, alachlor, butachlor, metolachlor and S-metolachlor; cyclohexene oxime herbicides such as sethoxydim; dinitroaniline herbicides such as benfluralin, ethalfluralin, pendimethalin, and trifluralin; nitrile herbicides such asbromoxynil octanoate; phenoxyacetic herbicides such as 4-CPA, 2,4-D, 3,4-DA, MCPA, and MCPA-thioethyl; phenoxybutyric herbicides such as 4-CPB, 2,4-DB, 3,4-DB, and MCPB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as cyhalofop, fluazifop, fluazifop-P, haloxyfop, haloxyfop-R; pyridine herbicides such as aminopyralid, clopyralid, fluroxypyr, picloram, and triclopyr; triazole herbicides such as carfentrazone ethyl; and the like.

The herbicides can also generally be employed in combination with known herbicide safeners such as: benoxacor, cloquintocet, cyometrinil, daimuron, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, MG191, MON4660, R29148, mephenate, naphthalic anhydride, N-phenylsulfonylbenzoic acid amides and oxabetrinil.

Exemplary fungicides which can be used in the oil-in-water emulsion of the present invention include, but are not limited to, difenoconazole, dimethomorph, dinocap, diphenylamine, dodemorph, edifenphos, fenarimol, fenbuconazole, fenpropimorph, myclobutanil, oleic acid (fatty acids), propiconazole, tebuconazole and the like.

It is understood by those skilled in the art that any combination of agriculturally active compounds may also be used in the oil-in-water emulsion of the present invention as long as a stable and effective emulsion is still obtained.

The amount of agriculturally active ingredient within the oil-in-water emulsion will vary depending upon the actual active ingredient, the application of the agriculturally active ingredient and the appropriate application levels which are well known to those skilled in the art. Typically, the total amount of agriculturally active ingredient within the oil-in-water emulsion will be from about 1, generally from about 5, preferably from about 10, more preferably from about 15 and most preferably from about 20 to about 45, generally to about 40, preferably to about 35 and most preferably to about 30 weight percent based on the total weight of the oil-in-water emulsion.

The polymeric modifier may be included in the oil phase to retard crystallization of the agriculturally active ingredient. The polymeric modifier permits the use of agriculturally active ingredients that have melting points below about 95 degrees Celsius. Examples of such agriculturally active ingredients that may be used in the oil-in-water emulsion composition of the present disclosure include Fluroxpyr Meptyl, Chloropyrifos, Chlorpyrifos methyl, Trifluralin, Cyhalofop butyl, Ethalfluralin, Benfluralin, Myclobutanil, Acequinocyl, Alpha-cypermethrin, Amitraz, Bensultap, Beta-cyfluthrin, Beta-cypermethrin, Bifenox, Bifenthrin, Bioresmethrin, Bromoxynil Octanoate, Butralin, Cyflufenamid, Cyfluthrin, Cypermethrin, Diclofop-methyl, Dicofol, Esfenvalerate, Ethalfluralin, Etofenprox, Fenazaquin, Fenoxaprop-P-ethyl, Fenpropathrin, Fenvalerate, Flumiclorac-pentyl, Fluoroglycofen-ethyl, Flurazole, Haloxyfop-etotyl, Indoxacarb, Lambda-cyhalothrin, Metamifop, Methoxychlor, Oxyfluorfen, Pendimethalin, Permethrin, Propaquizafop, Pyributicarb, Quizalofop-P-ethyl, Trifloxystrobin, Bromophos, Fenoxaprop-ethyl, Fluazolate, Nitrofen, and Profluralin.

Suitable polymeric modifiers for addition to the oil phase have very low water solubility and good solubility in a mixture of the active ingredient in a molten state with or without additional solvent present. Examples of suitable polymeric modifiers may include ethyl cellulose, for example, Ethocel 10 Std FP, Ethocel Std 4, Ethocel Std 7, Ethocel 45, Ethocel 100 FP, and Ethocel 300; Polyacrylate, Latex, Polycarbonate, Polyvinyl Acetate homopolymers and copolymers, Polyolefin, Polyurethane, Polyisobutylene, Polybutene, Vinyl polymers, Polyester, Polyether, and Polyacrylonitrile.

The components of the oil-in-water emulsion are combined using a process described below to produce oily globules having a lamellar liquid crystal coating. The lamellar liquid crystal coating is an extremely fine mono- or oligolamellar layer. Oligolamellar layer is understood to refer to a layer comprising from 2 to 5 lipid lamellae. This lamellar liquid crystal coating can be detected by Transmission Electronic Microscopy after cryofracture or negative stain, X-Ray diffraction or Optical Microscopy under polarized light. Terms and structure of lamellar crystal liquid phase are well defined in "The Colloidal Domain" second edition, by D. Fennell Evans and H. Wennerstrom, Wiley-VCH (1999), pages 295-296 and 306-307. The oligolamellar layer is comprised of the non-ionic lipophilic, non-ionic hydrophilic, and ionic surface-active agents, as stated previously. Preferably, the lipophilic surface-active agent and the hydrophilic surface-active agent each contain at least one optionally saturated and/or branched fatty hydrocarbon chain having more than 12 carbon atoms, preferably from 16 to 22 carbon atoms.

Preferably, the lipophilic surface-active agent has an HLB between about 2 and about 5. HLB is a standard term known to those skilled in the art and refers to Hydrophilic Lipophilic Balance which identifies the emulsifier's solubility in water or oil.

Lipophilic describes the ability of a material to dissolve in a fat-like solvent or lipid. The lipophilic surface-active agent is typically selected from optionally ethoxylated mono- or polyalkyl ethers or esters of glycerol or polyglycerol, mono- or polyalkyl ethers or esters of sorbitan (optionally ethoxylated), mono- or polyalkyl ethers or esters of pentaerythritol, mono- or polyalkyl ethers or esters of polyoxyethylene, and mono- or polyalkyl ethers or esters of sugars. Examples of lipophilic surface-active agents include, but are not limited to sucrose distearate, diglyceryl distearate, tetraglyceryl tristearate, decaglyceryl decastearate, diglyceryl monostearate, hexaglyceryltristearate, decaglyceryl pentastearate, sorbitan monostearate, sorbitan tristearate, diethylene glycol monostearate, the ester of glycerol and palmitic and stearic acids, polyoxyethylenated monostearate 2 EO (containing 2 ethylene oxide units), glyceryl mono- and dibehenate and pentaerythritol tetrastearate.

Hydrophilic describes the affinity of a material to associate with water. The hydrophilic surface-active agent typically has a HLB of from about 8 to about 12 and are typically selected from mono- or polyalkyl ethers or esters of polyethoxylated sorbitan, mono- or polyalkyl ethers or esters of polyoxyethylene, mono- or polyalkyl ethers or esters of polyglycerol, block copolymers of polyoxyethylene with polyoxypropylene or polyoxybutylene, and mono- or polyalkyl ethers or esters of optionally ethoxylated sugars. Examples of hydrophilic surface-active agents include, but are not limited to polyoxyethylenated sorbitan monostearate 4 EO, polyoxyethylenated sorbitan tristearate 20 EO, polyoxyethylenated sorbitan tristearate 20 EO, polyoxyethylenated monostearate 8 EO, hexaglyceryl monostearate, polyoxyethylenated monostearate 10 EO, polyoxyethylenated distearate 12 EO and polyoxyethylenated methylglucose distearate 20 EO.

In addition to the lipophilic and hydrophilic surface-active agents, an ionic surface-active agent also comprises the oligolamellar layer of the lamellar liquid crystal coating.

Ionic surface-active agents which can be used in the oil-in-water emulsion of the present invention include (a) neutralized anionic surface-active agents, (b) amphoteric surface-active agents, (c) alkylsulphonic derivatives and (d) cationic surface-active agents.

Neutralized anionic surface-active agents (a) include, but are not limited to, for example:
- alkali metal salts of dicetyl phosphate and dimyristyl phosphate, in particular sodium and potassium salts;
- alkali metal salts of cholesteryl sulphate and cholesteryl phosphate, especially the sodium salts;
- lipoamino acids and their salts, such as mono- and disodium acylglutamates, such as the disodium salt of N-stearoyl-L-glutamic acid, the sodium salts of phosphatidic acid;
- phospholipids; and
- the mono- and disodium salts of acylglutamic acids, in particular N-stearoylglutamic acid.

Anionic surface-active agents chosen from alkyl ether citrates and mixtures thereof which can be used in the oil-in-water emulsions of the present invention are disclosed in U.S. Pat. No. 6,413,527, which is incorporated herein by reference. Alkyl ether citrates include monoesters or diesters formed by citric acid and at least one oxyethylenated fatty alcohol comprising a saturated or unsaturated, linear or branched alkyl chain having from 8 to 22 carbon atoms and comprising from 3 to 9 oxyethylene groups, and mixtures thereof. These citrates can be chosen, for example from the mono- and diesters of citric acid and of ethoxylated lauryl alcohol comprising from 3 to 9 oxyethylene groups. The alkyl ether citrates are preferably employed in the neutralized form at a pH of about 7. Neutralization agents can being chosen from inorganic bases, such as sodium hydroxide, potassium hydroxide or ammonia, and organic bases, such as mono,- di- and triethanolamine, aminomethyl-1,3-propanediol, N-methylglucamine, basic amino acids, such as arginine and lysine and mixtures thereof.

Amphoteric surface-active agents (b) include, but are not limited to phospholipids and especially phosphatidylethanolamine from pure soya.

Alkylsulphonic derivatives (c) include, but are not limited to compounds of the formula:

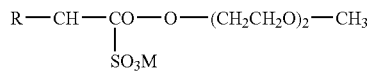

in which R represents the radicals $C_{16}H_{33}$ and $C_{18}H_{37}$, taken as a mixture or separately, and M is an alkali metal, preferably sodium.

Cationic surface-active agents (d) include but are not limited to surface-active agents as disclosed in U.S. Pat. No. 6,464,990, which is incorporated herein by reference. They are typically selected from the group of quaternary ammonium salts, fatty amines and salts thereof. The quaternary ammonium salts include, for example: those which exhibit the following formula:

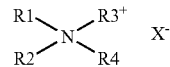

wherein the R1 to R4 radicals, which can be identical or different, represent a linear or branched aliphatic radical comprising from 1 to 30 carbon atoms or an aromatic radical, such as aryl or alkylaryl. The aliphatic radicals can comprise heteroatoms, such as oxygen, nitrogen, sulfur and halogens. The aliphatic radicals include alkyl, alkoxy, polyoxy($C_2$-$C_6$)alkylene, alkylamido, ($C_{12}$-$C_{22}$)alkyl-amido($C_2$-C6) alkyl, ($C_{12}$-$C_{22}$)alkyl acetate and hydroxyalkyl radicals comprising approximately from 1 to 30 carbon atoms; X is an anion selected from halides, phosphates, acetates, lactates, ($C_2$-$C_6$)alkyl sulfates, and alkyl- or alkylarylsulfonates. Preference is given, as quaternary ammonium salts to tetraalkylammonium chlorides, such as dialkyldimethylammonium and alkyltrimethylammonium chlorides in which the alkyl radical comprises approximately from 12 to 22 carbon atoms, in particular behenyltrimethylammonium, distearyldimethylammonium, cetyltrimethylammonium and benzyldimethylstearylammonium chlorides, or alternatively, stearamidopropyldimethyl(myristyl acetate) ammonium chloride; imidazolinium quaternary ammonium salts, such as those of formula:

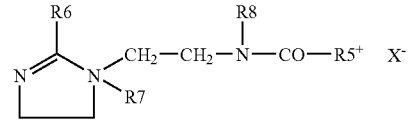

wherein R5 represents an alkenyl or alkyl radical comprising from 8 to 30 carbon atoms, for example derived from tallow fatty acids; R6 represents a hydrogen atom, an alkyl radical comprising from 1 to 4 carbon atoms or an alkenyl or alkyl radical comprising from 8 to 30 carbon atoms; R7 represents an alkyl radical comprising from 1 to 4 carbon atoms; R8 represents a hydrogen atom or an alkyl radical comprising from 1 to 4 carbon atoms; and X is an anion selected from the group of the halides, phosphates, acetates, lactates, alkyl sulfates, or alkyl, and alkylarylsulfonates. R5 and R6 preferably denote a mixture of alkenyl or alkyl radicals comprising from 12 to 21 carbon atoms, for example derived from tallow fatty acids, R7 preferably denotes a methyl radical and R8 preferably denotes hydrogen. Quaternary diammonium salts are also contemplated, such as propanetallowdiammonium dichloride.

Fatty amines include, but are not limited to those of formula:

wherein R9 is an optionally saturated and/or branched hydrocarbon chain, having between 8 and 30 carbon atoms, preferably between 10 and 24 carbon atoms; R10 and R11 are selected from H and an optionally saturated and/or branched hydrocarbon chain, having between 1 and 10 carbon atoms; preferably between 1 and 4 carbon atoms; m is an integer between 1 and 10 and is preferably between 1 and 5; and n is either 0 or 1.

Examples of fatty amines include, but are not limited to, stearylamine, aminoethyl-ethanolamide stearate, diethylenetriamine stearate, palmitamidopropyldimethyl-amine, palmitamidopropyldiethylamine, palmitamidoethyldiethylamine, palmitamidoethyldimethylamine. Commercially available fatty amines include, but are not limited to, Incromine™ BB from Croda, Amidoamine™ MSP from Nikkol, and Lexamine™ series from Inolex, the Acetamine series from Kao Corp; Berol 380, 390, 453 and 455, and Ethomeen™ series from Akzo Nobel, and Marlazin™ L10, OL2, OL20, T15/2, T50 from Condea Chemie.

As described above, the surface-active agents form the lamellar liquid crystal coating of the oily globules suspended within the aqueous phase of the oil-in-water emulsion of the present invention. The amount of the three surface-active agents utilized in the oil-in-water emulsion of the present invention is typically from about 20, preferably from about 35 to about 65, preferably to about 55 weight percent of non-ionic lipophilic surface-active agent, from about 15, preferably from about 25 to about 50, preferably to about 40 weight percent of non-ionic hydrophilic surface-active agent and from about 5, preferably from about 10 to about 45, preferably to about 35 weight percent of ionic surface-active agent; based on the total combined weight of surface active agents. The coating of the oily globules comprises a total amount of hydrophilic surface-active agent, lipophilic surface-active agent and ionic surface-active agent to be between about 2 and about 20 percent by weight, based on the total weight of the oil-in-water emulsion. Preferably the total amount is from about 2.5, more preferably from about 3 to 10, more preferably to about 6 weight percent, based on the total weight of the oil-in-water emulsion.

The ratio of the total weight of the surface-active compounds to the total weight of oil is typically from 1:2.5 to 1:25.

The amount of the polymeric modifier utilized in the oil-in-water emulsion of the present disclosure is typically from about 0.2, preferably from about 2 to about 40, preferably to about 20 weight percent based on the total weight of the oil-in-water emulsion.

The aqueous phase is typically water, for example, deionized water. The aqueous phase may also contain other additives such as compounds that lower the freezing point, for example alcohols, e.g. isopropyl alcohol and propylene glycol; pH buffering agents, for example alkali phosphates such as sodium phosphate monobasic monohydrate, sodium phosphate dibasic; biocides, for example Proxel GXL; and antifoams, for example octamethylcyclotetrasiloxane (Antifoam A from Dow Corning). Other additives and/or adjuvants can also be present in the aqueous phase as long as the stability of the oil-in-water emulsion is still maintained. Other additives also include water-soluble agriculturally active compounds.

The oil phase or the coated oily globules are from 5, preferably from 8 and more preferably from 10 to 50 percent, preferably to 45 and most preferably to 40 weight percent, based on the total weight of the oil-in-water emulsion composition. The oil/water ratio is typically less than or equal to 1.

Other additives and/or adjuvants can also be present within the oil-in-water emulsion of the present invention, as long as the stability and activity of the oil-in-water emulsion is still obtained. The oil-in-water emulsions of the present invention may additionally contain adjuvant surface-active agents to enhance deposition, wetting and penetration of the agriculturally active ingredient onto the target site, e.g. crop, weed or organism. These adjuvant surface-active agents may optionally be employed as a component of the emulsion in either the oil or water phase, or as a tank mix component; the use of and amount desired being well known by those skilled in the art. Suitable adjuvant surface-active agents include, but are not limited to ethoxylated nonyl phenols, ethoxylated synthetic or natural alcohols, salts of the esters or sulphosuccinic acids, ethoxylated organosilicones, ethoxylated fatty amines and blends of surface-active agents with mineral or vegetable oils.

The oil-in-water emulsion of the present invention can be prepared according to the process described in U.S. Pat. No. 5,925,364, the teachings of which are incorporated herein by reference. The agriculturally active ingredient or a combination of agriculturally active ingredients is first melted or dissolved into the polymeric modifier, adding solvent if desired, after which the nonionic surface-active agent(s) is dissolved into the mixture. The then mixture is homogenized by cavitation using a high pressure homogenizer, to provide the small particle sized oily globules. The mean size of the coated oily globules is typically less than 800 nanometers, preferably less than 500 nanometers and most preferably about 200 nanometers, as determined using laser diffraction particle size analysis and scanning electron microscopy.

In one embodiment, the oil-in-water emulsion is prepared by:
1) melting or dissolving an agriculturally active ingredient(s) into the polymeric modifier and optionally a suitable solvent;
2) mixing an oil phase, comprising the lipophilic surfactant, the polymeric modifier containing the dissolved agriculturally active ingredient(s), the hydrophilic surfactant, the ionic surfactant, an agriculturally active compound and optionally a suitable solvent and (B) an aqueous phase to obtain a mixture; and
3) homogenizing the mixture by subjecting the mixture to cavitation.

In the first step, the mixture can be formed by conventional stirring, for example, using a high shear homogenizer rotating at a rate of approximately between 2000 and 7000 rpm for a time approximately between 5 and 60 minutes and at a temperature between approximately 20° C. and 95° C.

The homogenization can be performed by using a high pressure homogenizer operating at pressures between approximately 200 and 1000 bar as is well known to those skilled in the art. The process is performed by successive passages, generally from 2 to 12 passages, at a selected pressure; the mixture being returned to normal pressure between each passage. The homogenization of the second step may also be carried out under the action of ultrasound or alternatively by the use of a homogenizer equipped with a rotor-stator type head.

Another embodiment of the present invention is the use of the oil-in-water emulsion in agricultural applications to control, prevent or eliminate unwanted living organisms, e.g. fungi, weeds, insects, bacteria or other microorganisms and other pests. This would include its' use for protection of a plant against attack by a phytopathogenic organism or the treatment of a plant already infested by a phytopathogenic organism, comprising applying the oil-in-water emulsion composition, to soil, a plant, a part of a plant, foliage, flowers, fruit, and/or seeds in a disease inhibiting and phytologically acceptable amount. The term "disease inhibiting and phytologically acceptable amount" refers to an amount of a compound that kills or inhibits the plant disease for which control is desired, but is not significantly toxic to the plant. The exact concentration of active compound required varies with the fungal disease to be controlled, the type of formulations employed, the method of application, the particular plant species, climate conditions, and the like, as is well known in the art.

Additionally, the oil-in-water emulsions of the present invention are useful for the control of insects or other pests, e.g. rodents. Therefore, the present invention also is directed to a method for inhibiting an insect or pest which comprises applying to a locus of the insect or pest an oil-in-water emulsion comprising an insect-inhibiting amount of an agriculturally active compound for such use. The "locus" of insects or pests is a term used herein to refer to the environment in which the insects or pests live or where their eggs are present, including the air surrounding them, the food they eat, or objects which they contact. For example, insects which eat or contact edible or ornamental plants can be controlled by applying the active compound to plant parts such as the seed, seedling, or cutting which is planted, the leaves, stems, fruits, grain, or roots, or to the soil in which the roots are growing. It is contemplated that the agriculturally active compounds and oil-in-water emulsions containing such, might also be useful to protect textiles, paper, stored grain, seeds, domesticated animals, buildings or human beings by applying an active compound to or near such objects. The term "inhibiting an insect or pest" refers to a decrease in the numbers of living insects or pests, or a decrease in the number of viable insect eggs. The extent of reduction accomplished by a compound depends, of course, upon the application rate of the compound, the particular compound used, and the target insect or pest species. At least an inactivating amount should be used. The terms "insect or pest-inactivating amount" are used to describe the amount, which is sufficient to cause a measurable reduction in the treated insect or pest population, as is well known in the art.

The locus to which a compound or composition is applied can be any locus inhabited by an insect, mite or pest, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Additionally, the present invention relates to the use of oil-in-water emulsions comprising agriculturally active compounds which are herbicides. The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include emerging seedlings and established vegetation.

Herbicidal activity is exhibited when they are applied directly to the locus of the undesirable plant thereof at any stage of growth or before emergence of the weeds. The effect observed depends upon the plant species to be controlled, the stage of growth of the plant, the particle size of solid components, the environmental conditions at the time of use, the specific adjuvants and carriers employed, the soil type, and the like, as well as the amount of chemical applied. These and other factors can be adjusted as is known in the art to promote selective herbicidal action. Generally, it is preferred to apply such herbicides post emergence to relatively immature undesirable vegetation to achieve the maximum control of weeds.

Another specific aspect of the present invention is a method of preventing or controlling pests such as nematodes, mites, arthropods, rodents, termites, bacteria or other microorganisms, comprising applying to a locus where control or prevention is desired a composition of the present invention which comprises the appropriate active compound such as a nematocide, miticide, arthropodicide, rodenticide, termiticide or biocide.

The actual amount of agriculturally active compound to be applied to loci of disease, insects and mites, weeds or other pests is well known in the art and can readily be determined by those skilled in the art in view of the teachings above.

The composition of the present invention surprisingly offers stable agricultural oil-in-water emulsions having low viscosity and long term shelf life. Additionally, the stable agricultural oil-in-water emulsions of the present invention can offer other surprising improvements, e.g. efficacy.

The following examples are provided to illustrate the present invention. The examples are not intended to limit the scope of the present invention and they should not be so interpreted. Amounts are in weight parts or weight percentages unless otherwise indicated.

EXAMPLES

These examples are provided to further illustrate the invention and are not meant to be construed as limiting.

As disclosed herein, all temperatures are given in degrees Celsius and all percentages are weight percentages unless otherwise stated. The active ingredients in all examples are super-saturated.

In these examples, the process is performed using the following procedure:

The solid agriculturally active ingredient is melted or dissolved into the polymeric modifier. The polymeric modifier is then mixed into the oil phase A. The oil phase A and the aqueous phase B are heated separately to the desired temperature. Phase B is poured into Phase A, with stirring of 4000-8000 rpm provided by a Silverson L4RT high shear homogenizer fitted with a square hole high shear screen. Stirring and temperature conditions are maintained for 10 minutes.

The mixture is then introduced into a Niro Soavi high pressure 2-stage homogenizer of type Panda 2K, which is adjusted to a pressure of 1000 bar for 2 to 12 successive passages.

A stabilized oil-in-water emulsion is thus obtained, the oily globules of which have a mean diameter of typically around 200 nm.

Example 1

Fluroxypyr MHE Oil-in-Water Emulsion

| | |
|---|---|
| Fluroxypyr methylheptyl ester | 27.29 |
| Ethocel 10 Std FP | 2.73 |
| Diglycerol monostearate (Nikkol DGMS by Nikko Chemical Co.) | 2.70 |
| Sorbitan (40EO) stearate (Tween 61 by Uniqema) | 2.03 |
| Oil (AMD 810) | 12.12 |
| Aqueous Phase B | |
| Deionized water | 42.30 |
| Proxel GLX Biocide | 0.10 |

|  | wt % |
|---|---|
| Cedepal TD-407 | 0.73 |
| Glycerin | 10.00 |

The samples showed no sign of crystal formation, creaming, or settling after 10 weeks at 0° C. and room temperature. The size of the oily globules in the oil-in-water emulsion as determined by a Malvern Zetasizer was 242 nm. The oil-in-water emulsion was stable under accelerated storage test conditions of 10 weeks at Freeze/Thaw (temperature cycled daily from −10° C. to 40° C.) and 54° C. with no change in the size of the oily globules and no sedimentation or syneresis.

Example 2

Fluroxypyr MHE Oil-in-Water Emulsion

|  | wt % |
|---|---|
| Oil Phase A |  |
| Fluroxypyr methylheptyl ester | 27.29 |
| Ethocel 100FP | 2.73 |
| Diglycerol monostearate (Nikkol DGMS by Nikko Chemical Co.) | 2.70 |
| Sorbitan (40EO) stearate (Tween 61 by Uniqema) | 2.03 |
| Oil (AMD 810) | 12.12 |
| Aqueous Phase B |  |
| Deionized water | 48.30 |
| Proxel GLX Biocide | 0.10 |
| Cedepal TD-407 | 0.73 |
| Propylene Glycol | 4.00 |

The size of the oily globules in the oil-in-water emulsion as determined by a Malvern Zetasizer was 410 nm. The samples showed no sign of crystal formation, creaming, or settling after 10 weeks at 0° C. and room temperature. The oil-in-water emulsion was stable under accelerated storage test conditions of 10 weeks at Freeze/Thaw (temperature cycled daily from −10° C. to 40° C.) and 54° C. with no change in the size of the oily globules and no sedimentation or syneresis.

Example 3

Fluroxypyr MHE Oil-in-Water Emulsion

|  | wt % |
|---|---|
| Oil Phase A |  |
| Fluroxypyr methylheptyl ester | 25.9 |
| Ethocel Std 7 | 2.6 |
| Diglycerol monostearate (Nikkol DGMS by Nikko Chemical Co.) | 2.6 |
| Sorbitan (40EO) stearate (Tween 61 by Uniqema) | 1.9 |
| Oil (AMD 810) | 11.5 |
| Aqueous Phase B |  |
| Deionized water | 54.2 |
| Sodium phosphate, diabasic | 0.3 |
| Sodium phosphate, monobasic monohydrate | 0.2 |
| Proxel GLX Biocide | 0.3 |
| n-Stearoyl glutamic acid di-sodium salt (Amisoft HS-21P by Ajinomoto) | 0.5 |

The samples showed no sign of crystal formation, creaming, or settling after two weeks at room temperature. The size of the oily globules in the oil-in-water emulsion as determined by a Malvern Zetasizer was 190 nm. The oil-in-water emulsion was stable under accelerated storage test conditions of 2 weeks at room temperature, 40° C., and 54° C. with no change in the size of the oily globules and no sedimentation or syneresis.

Example 4

Trifluralin Oil-in-Water Emulsion

|  | wt % |
|---|---|
| Oil Phase A |  |
| Trifluralin | 24.0 |
| Ethocel Std 4 | 2.4 |
| Diglycerol monostearate (Nikkol DGMS by Nikko Chemical Co.) | 2.6 |
| Sorbitan (40EO) stearate (Tween 61 by Uniqema) | 1.9 |
| Genigen 4166 | 9.6 |
| Aqueous Phase B |  |
| Deionized water | 51.2 |
| n-Stearoyl glutamic acid di-sodium salt (Amisoft HS-21P by Ajinomoto) | 0.5 |
| Proxel GXL Biocide | 0.3 |
| 1,2-propanediol | 7.5 |

The samples showed no sign of crystal formation, creaming, or settling after two weeks at room temperature. The size of the oily globules in the oil-in-water emulsion as determined by a Malvern Mastersizer was 185 nm. The oil-in-water emulsion was stable under accelerated storage test conditions of 2 weeks at 40° C. and 54° C. with no change in the size of the oily globules and no sedimentation or syneresis.

Example 5

Chlorpyrifos Oil-in-Water Emulsion

|  | wt % |
|---|---|
| Oil Phase A |  |
| Chloropyrifos | 10.0 |
| Ethocel 4S | 1.0 |
| Genigen 4166 | 2.4 |
| Sorbitan (40EO) stearate (Tween 61 by Uniqema) | 1.5 |
| PEG 2 Stearyl ether | 2.0 |
| Aqueous Phase B |  |
| Deionized water | 82.6 |
| n-Stearoyl glutamic acid di-sodium salt (Amisoft HS-21P by Ajinomoto) | 0.5 |

The samples showed no sign of crystal formation, creaming, or settling after two weeks at room temperature. The size of the oily globules in the oil-in-water emulsion as determined by a Malvern Mastersizer was 190 nm. The oil-in-water emulsion was stable under accelerated storage test conditions of 2 weeks at 40° C. and 54° C. with no change in the size of the oily globules and no sedimentation or syneresis.

Example 6

Chlorpyrifos Oil-in-Water Emulsion

| | wt % |
|---|---|
| Oil Phase A | |
| Chloropyrifos | 20.0 |
| Ethocel 4S | 2.0 |
| Genigen 4166 | 4.8 |
| Sorbitan (40EO) stearate (Tween 61 by Uniqema) | 1.7 |
| PEG 2 Stearyl ether | 2.3 |
| Aqueous Phase B | |
| Deionized water | 61.1 |
| n-Stearoyl glutamic acid di-sodium salt (Amisoft HS-21P by Ajinomoto) | 0.6 |
| 1,2-Propylene glycol | 7.5 |

The samples showed no sign of crystal formation, creaming, or settling after two weeks at room temperature. The size of the oily globules in the oil-in-water emulsion as determined by a Malvern Mastersizer was 190 nm. Accelerated storage test conditions of 2 weeks at 40° C. led to a slight increase in the size of the oily globules to 200 nm.

What is claimed is:

1. An oil-in-water emulsion composition having an oil phase present as oily globules having a mean diameter about 200 nanometers or less suspended in a water phase, the oil phase comprising:
   a polymeric modifier being compatible with the oil phase, wherein the polymeric modifier is ethyl cellulose;
   at least one agriculturally active compound;
   at least one non-ionic lipophilic surface-active agent;
   at least one non-ionic hydrophilic surface-active agent; and
   at least one ionic surface-active agent;
   wherein the at least one agriculturally active compound exhibits decreased crystallization in the oil phase.

2. The composition of claim 1 wherein the non-ionic lipophilic surface-active agent has an Hydrophilic Lipophilic Balance of between 2 and 5.

3. The composition of claim 2, wherein the at least one non-ionic lipophilic surface-active agent is selected from the group consisting of:
   monoalkyl glycerol ethers, polyalkyl glycerol ethers, monoalkyl glycerol esters, polyalkyl glycerol esters, monoalkyl polyglycerol ethers, polyalkyl polyglycerol ethers, monoaklyl polyglycerol esters, polyalkyl polyglycerol esters, ethoxylated monoalkyl glycerol ethers, ethoxylated polyalkyl glycerol ethers, ethoxylated monoalkyl glycerol esters, ethoxylated polyalkyl glycerol esters, ethoxylated monoalkyl polyglycerol ethers, ethoxylated polyalkyl polyglycerol ethers, ethoxylated monoaklyl polyglycerol esters, ethoxylated polyalkyl polyglycerol esters, monoalkyl sorbitan ethers, polyalkyl sorbitan ethers, monoalkyl sorbitan esters, polyalkyl sorbitan esters, ethoxylated monoaklyl sorbitan ethers, ethoxylated polyaklyl sorbitan ethers, ethoxylated monoalkyl sorbitan esters, ethoxylated polyalkyl sorbitan esters, monoalkyl pentaerythritol ethers, polyalkyl pentaerythritol ethers, monoalkyl pentaerythritol esters, polyalkyl pentaerythritol esters, monoalkyl polyoxyethylene ethers, polyalkyl polyoxyethylene ethers, monoalkyl polyoxyethylene esters, polyalkyl polyoxyethylene esters, monoalkyl ether sugars, polyalkyl ether sugars, monoalkyl ester sugars, polyalkyl ester sugars, ethoxylated monoalkyl ether sugars, ethoxylated polyalkyl ether sugars, ethoxylated monoalkyl ester sugars, or ethoxylated polyalkyl ester sugars.

4. The composition of claim 3, wherein the non-ionic lipophilic surface-active agent is selected from the group consisting of sucrose distearate, diglyceryl distearate, tetraglyceryl tristearate, decaglyceryl decastearate, diglyceryl monostearate, hexaglyceryltristearate, decaglyceryl pentastearate, sorbitan monostearate, sorbitan tristearate, diethylene glycol monostearate, the ester of glycerol and palmitic and stearic acids, polyoxyethylenated monostearate 2 EO (containing 2 ethylene oxide units), glyceryl mono- and dibehenate and pentaerythritol tetrastearate.

5. The composition of claim 1, wherein the non-ionic hydrophilic surface-active agent has an Hydrophilic Lipophilic Balance between 8 and 12.

6. The composition of claim 5, wherein the at least one non-ionic hydrophilic surface-active agent is selected from the group consisting of:
   polyoxylated monoalkyl sorbitan ethers, polyoxylated polyalkyl sorbitan ethers, polyoxylated monoalkyl sorbitan esters, polyethoxylated polyalkyl sorbitan esters, monoalkyl polyoxyethylene ethers, polyalkyl polyoxyethylene ethers, monoalkyl polyoxyethylene esters, polyalkyl polyoxyethylene esters, monoalkyl polyglycerol ethers, polyalkyl polyglycerol ethers, monoalkyl polyglycerol esters, polyalkyl polyglycerol esters, block copolymers of polyoxyethylene with polyoxypropylene, block copolymers of polyoxyethylene with polyoxybutylene, monoalkyl ether sugars, polyalkyl ether sugars, monoalkyl ester sugars, polyalkyl ester sugars, ethoxylated monoalkyl ether sugars, ethoxylated polyalkyl ether sugars, ethoxylated monoalkyl ester sugars, or ethoxylated polyalkyl ester sugars.

7. The composition of claim 6, wherein the non-ionic hydrophilic surface-active agent is selected from the group consisting of polyoxyethylenated sorbitan monostearate 4 EO, polyoxyethylenated sorbitan tristearate 20 EO, polyoxyethylenated sorbitan tristearate 20 EO, polyoxyethylenated monostearate 8 EO, hexaglyceryl monostearate, polyoxyethylenated monostearate 10 EO, polyoxyethylenated distearate 12 EO and polyoxyethylenated methylglucose distearate 20 EO.

8. The composition of claim 1, wherein the ionic surface-active agent is selected from the group consisting of (a) neutralized anionic surface-active agents, (b) amphoteric surface-active agents, (c) alkylsulphonic derivatives and (d) cationic surface-active agents.

9. The composition of claim 8, wherein the at least one ionic surface-active agent is selected from the group consisting of:
   alkali metal salts of dicetyl phosphate, alkali metal salts of dimyristyl phosphate, alkali metal salts of cholesteryl sulphate, alkali metal salts of cholesteryl phosphate, lipoamino acids, lipoamino acid salts, monosodium acylglutamates, disodium acylglutamates, disodium salts of N-stearoyl-L-glutamic acid, sodium salts of phosphatidic acid, phospholipids, monosodium salts of acylglutamic acids, disodium salts of acylglutamic acids, N-stearoylglutamic acid, or alkyl ether citrates.

10. The composition of claim 8, wherein the ionic surface-active agent is a phospholipid.

11. The composition of claim 8, wherein the ionic surface-active agent is an alkylsulphonic derivative.

12. The composition of claim 8, wherein the ionic surface-active agent is selected from the group consisting of quaternary ammonium salts, fatty amines and salts thereof.

13. The composition of claim 1, wherein the agriculturally active compound is selected from a group consisting of fungicides, insecticides, nematocides, miticides, biocides, termiticides, rodenticides, arthropodicides, and herbicides.

14. A method of controlling or preventing fungal attack, comprising applying a composition of claim 13 to the fungus, soil, plant, root, foliage, seed or locus in which the infestation is to be prevented or controlled.

15. A method of inhibiting insects comprising applying to a locus where control or prevention is desired a composition of claim 13.

16. A method of preventing or controlling unwanted vegetation comprising applying to a locus where control or prevention is desired a composition of claim 13.

17. A method of preventing or controlling nematodes, comprising applying to a locus where control or prevention is desired a composition of claim 13.

18. A method of preventing or controlling mites, comprising applying to a locus where control or prevention is desired a composition of claim 13.

19. A method of preventing or controlling arthropods, comprising applying to a locus where control or prevention is desired a composition of claim 13.

20. A method of preventing or controlling bacteria and other microorganisms, comprising applying to a locus where control or prevention is desired a composition of claim 13.

21. A method of preventing or controlling rodents, comprising applying to a locus where control or prevention is desired a composition of claim 13.

22. A method of preventing or controlling termites, comprising applying to a locus where control or prevention is desired a composition of claim 13.

23. The composition of claim 1, wherein the oil-in-water emulsion composition is from about 1 to about 60 weight percent total oil phase, from about 0.2 to about 40 weight percent polymeric modifier, from about 1 to about 45 weight percent agriculturally active compound, from about 0.4 to about 13 weight percent non-ionic lipophilic surface-active agent, from about 0.3 to about 10 weight percent non-ionic hydrophilic surface-active agent, from about 0.1 to about 9 weight percent ionic surface-active agent, based on a total weight of the oil-in-water emulsion composition.

24. The composition of claim 9, wherein the metal in the alkali metal salts of dicetyl phosphate and dimyristyl phosphate is either sodium or potassium.

25. The composition of claim 9, wherein the metal in the alkali metal salts of cholesteryl sulphate and cholesteryl phosphate is sodium.

26. The composition of claim 9, wherein the lipoamino acid is the disodium salt of N-stearoyl-L-glutamic acid.

27. The composition of claim 9, wherein the acylglutamic acid is N-stearoylglutamic acid.

28. The composition of claim 1, wherein the at least one agriculturally active compound is melted or dissolved into the polymeric modifier and an optional solvent.

29. The composition of claim 1, wherein the polymeric modifier retards crystallization of the at least one agriculturally active compound having a melting point below about 95° C.

30. The composition of claim 1, wherein the oily globules have a mean diameter of about 200 nanometers.

* * * * *